US00PP08857P

United States Patent [19]

Vander Meer

[11] Patent Number: Plant 8,857

[45] Date of Patent: Aug. 9, 1994

[54] ROSE PLANT NAMED SELARGON

[75] Inventor: Peter J. A. Vander Meer, Carlsbad, Calif.

[73] Assignee: Terra Nigra B.V., De Kwakel, Netherlands

[21] Appl. No.: 208,213

[22] Filed: Mar. 10, 1994

[51] Int. Cl.[5] ..... A01H 5/00

[52] U.S. Cl. ..... Plt./12

[58] Field of Search ..... Plt. 12

*Primary Examiner*—James R. Feyrer
*Assistant Examiner*—Bruce R. Campbell

[57] ABSTRACT

A new and distinct greenhouse rose, particularly distinguished by its continuous and profuse production of medium, red-pink and creamy-white flowers borne singly on strong, upright stems on a sturdy bush of medium height having abundant foliage.

1 Drawing Sheet

1

The present invention relates to a new and distinctive variety of rose plant of the Hybrid Tea class, which was originated by my crossing Seedling 44.87 as the seed parent with "Shadow" (Selferr) as the pollen parent (plant patent number in The Netherlands 9132). Seedling 44.87 is not publicly available. It has a champagne color, a small flower, and a higher number of flowers than Selargon. "Shadow" (Selferr) differs by Selargon by its color (salmon-orange with creamy white), its longer stems, its better vase-life, and its lower number of flower-stems. Selargon was germinated in 1985, in De Kwakel, The Netherlands. The plant is the result of breeding efforts carried on by me since 1984. The new plant resulted from my breeding efforts to improve the quality, production, vase life, and to find new colors. The plant has been asexually reproduced by cuttings and grafting in a specific breeding area in the greenhouse of Terra Nigra B.V. in De Kwakel, The Netherlands. The methods of present propagation are tissue-culture and grafting. Selargon has been in commerce in The Netherlands since 1988. Of the many cultivars known to me, there is no cultivar sufficiently similar to Selargon so as to provide a meaningful basis for comparison. Among the novel characteristics possessed by the new variety which distinguish it from its parents and all other varieties of which I am aware are:

(1) medium-large distinct red-pink and creamy-white flowers (2) continuous and profuse production of flowers (whole year round)

(3) strong and upright green flower stem (4) upright plant of medium height with abundant foliage (5) very good vase-life The accompanying drawing shows typical specimens of the vegetative growth and flowers of the new variety in different stages of development and as depicted in color as nearly true as it is reasonably possible to make the same in a color illustration of this character. The following is a detailed description of my new variety, with color terminology in accordance with The Royal Horticultural Society Colour Chart (R.H.S.C.C.). The terminology used in the color description herein refers to plate numbers in the aforementioned color chart, e.g. "28B" is plate "28B" of The Royal Horticultural Society Colour Chart.

2

FLOWER

Blooming habit: Normally borne singly, one per stem. However, some disbudding is required.

A. Bud:

(1) *Size.*—medium. Diameter of 2 cm. Depth or length of 3 cm.

(2) *Form.*—Ovoid, opens normal.

(3) *Sepals.*—When the sepals first divide, the petal color is cream with red edge. Sepal color is green (outside 143C, inside 141C). color at maturity is the same. (outside 143C, inside 141C). Number of sepals: 5. Shape of sepals: Pointed. No extensions above the bud. Striae: No. Calyx: Pear shaped. The aspect is smooth. Size Calyx: broad.

B. Bloom:

Blooming habit: Continuous, profusely whole year blooming.

(1) *Size.*—Medium — diameter of 9 cm and depth of 3 cm.

(2) *Form.*—First open: cup form. mature: first the shape is round, then opens totally.

(3) *Petalage.*—30–40 petals.

C. Petals:

(1) *Texture.*—Semi leathery.

(2) *Appearance.*—Adaxial surface: satiny. Abaxial surface: smooth.

(3) *Arangement.*—Normal.

(4) *Outer petals.*—Shape: Round. Width: About 4 cm. Basal attachment: About 5 mm. Coloration: Adaxial surface: red 45B Abaxial surface: cream 8D to 15D, with occasional blush of 54B-C. Character: Reflexed.

(5) *Inner petals.*—Shape: Slightly smaller than outer petals. Width: About 3–3.5 cm. Basal attachment: About 5 mm. Coloration: Similar to or darker than outer petals, with stronger blush on abaxial surface.

(6) *Petaloids.*—Number: About 10. Shape: Variable. Width: About 1.5 cm. Coloration: Substantially identical to petals.

(7) *Persistence.*—Remain attached to receptacle for 9 days or longer.

(8) *Fragrance.*—Slight.

REPRODUCTIVE ORGANS

A. Stamens:

(1) *Arrangement.*—In a circle around the pistils.
(2) *Number.*—Average 130–140.
(3) *Filaments.*—Length 5–7 mm. Color: yellow 16A.
(4) *Anthers.*—Size 3 mm. Color: creamy yellow 16D.
(5) *Pollen.*—Yellow 16C.

B. Pistils:
(1) *Number.*—80–90.
(2) *Styles.*—Length: 8 mm. Color: creamy-red 8D-44B.
(3) *Stigma.*—Creamy yellow 16D.
(4) *Ovaries.*—Pear shaped.

HIPS

A.
(1) *Color.*—Orange at maturity.
(2) *Shape.*—Round.
(3) *Fertility.*—The fruit is not very fertile. The seeds are retained within the hips.

PLANT

A. Form: Upright and branched.
B. Growth: Very fast, average height after one year is 60–70 cm.
C. Foliage: 7–9 leaves on a stem.
(1) *Size.*—Average 14 cm (7-leave).

(2) *Shape.*—Oval pointed.
(3) *Margin type.*—Serrated.
(4) *Texture.*—Smooth.
(5) *Color.*—Upperside: dark green 139A. Underside: soft green 191B.
(6) *Leaflets.*—Average 5 or 7. size: 5–7 cm.
(7) *Stipules.*—Some.
(8) *Rachis.*—7 cm from upper leaf to flower bottom. Color: green 147D.
(9) *Petiolule.*—1–2 mm.
(10) *Petioles.*—Length of 8 cm from stem to the end of leaf.
(11) *Ribs.*—Creamy green 145D.

D. Thorns: The plant has a normal number of thorns and few prickles at the petioles.

E. Stem:
(1) *Length basel stem.*—40–50 cm.
(2) *Color.*—green 144A.
(3) *Quality.*—strong and upright.

I claim:

1. A new and distinct variety of greenhouse rose, substantially as herein shown and described, characterized by its continuous and profuse production of medium, red-pink and creamy-white flowers borne singly on strong, upright stems on a sturdy bush of medium height having abundant foliage.

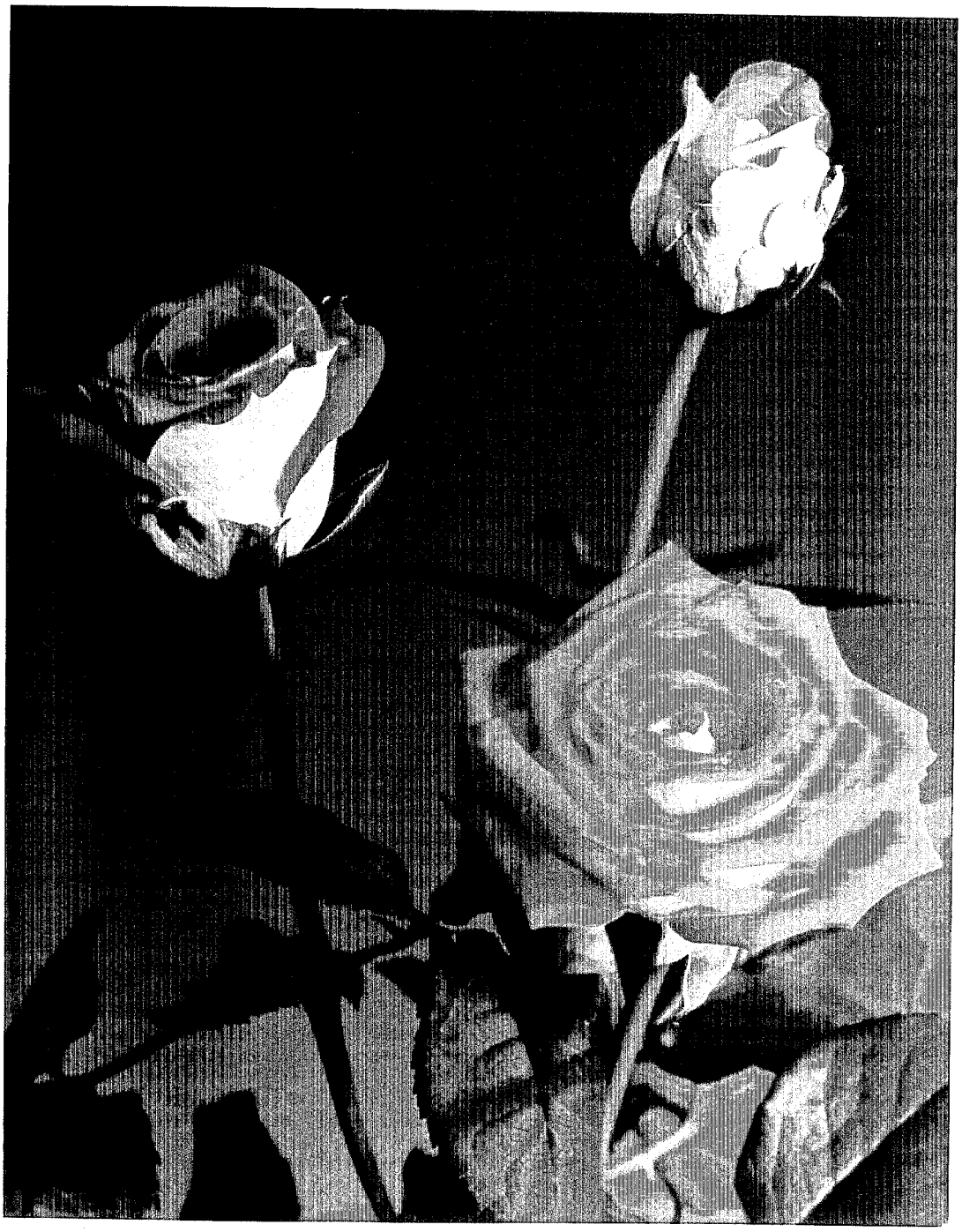

* * * * *